United States Patent
Benner et al.

(10) Patent No.: US 9,636,039 B2
(45) Date of Patent: May 2, 2017

(54) METHOD AND APPARATUS TO ACQUIRE MAGNETIC RESONANCE IMAGES IN A SESSION, WITH ACQUISITION OF A CONSISTENTLY VALID REFERENCE SCAN

(71) Applicant: Siemens Aktiengesellschaft, Munich (DE)

(72) Inventors: Thomas Benner, Erlangen (DE); Andre Jan Willem Van Der Kouwe, Woburn, MA (US)

(73) Assignees: Siemens Aktiengesellschaft, Munich (DE); Massachusetts General Hospital Corporation, Boston, MA (US)

( * ) Notice: Subject to any disclaimer, the term of this patent is extended or adjusted under 35 U.S.C. 154(b) by 166 days.

(21) Appl. No.: 14/454,028

(22) Filed: Aug. 7, 2014

(65) Prior Publication Data

US 2016/0038054 A1    Feb. 11, 2016

(51) Int. Cl.
A61B 5/055       (2006.01)
A61B 5/11        (2006.01)
A61B 5/00        (2006.01)
G01R 33/54       (2006.01)
G01R 33/565      (2006.01)

(52) U.S. Cl.
CPC ............ *A61B 5/055* (2013.01); *A61B 5/0037* (2013.01); *A61B 5/1128* (2013.01); *G01R 33/543* (2013.01); *G01R 33/56509* (2013.01)

(58) Field of Classification Search
CPC ..... A61B 5/0037; A61B 5/055; A61B 5/1128; G01R 33/288
See application file for complete search history.

(56) References Cited

U.S. PATENT DOCUMENTS 6,259,250 B1 * 7/2001 Mock ................. G01R 33/5615
                                                  324/300
2014/0077811 A1 * 3/2014 Lin ......................... A61B 5/055
                                                  324/309

* cited by examiner

*Primary Examiner* — Michael Rozanski
(74) *Attorney, Agent, or Firm* — Schiff Hardin LLP

(57) ABSTRACT

In a magnetic resonance (MR) imaging method and apparatus, multiple diagnostic scans are obtained of an examination subject during an imaging session. An initial reference scan of the subject is obtained at the beginning of the session and, as the session proceeds, an automatic determination is made before each diagnostic scan is obtained as to whether the immediately preceding reference scan is still valid, primarily be checking whether an amount of patient movement has occurred that renders the immediately preceding reference scan invalid. Either a new reference scan is obtained before the next diagnostic scan, or, if still valid, the immediately preceding reference scan is used for the next diagnostic scan.

4 Claims, 4 Drawing Sheets

METHOD AND APPARATUS TO ACQUIRE MAGNETIC RESONANCE IMAGES IN A SESSION, WITH ACQUISITION OF A CONSISTENTLY VALID REFERENCE SCAN

BACKGROUND OF THE INVENTION

Field of the Invention

The present invention concerns a method to operate a magnetic resonance imaging apparatus in order to acquire multiple images in a session, wherein a reference scan is acquired that is used by the technician implementing the imaging session to ensure that all of the images in the session are acquired so as to be consistent with prescribed imaging conditions. The invention also concerns a magnetic resonance imaging apparatus to implement such a method.

Description of the Prior Art

Before acquiring a magnetic resonance (MR) diagnostic image (i.e., an MR image having an image content and quality of a sufficiently high level to permit a reliable medical diagnosis to be made therefrom), it is common to first acquire a localizer or scout (reference) scan of the examination subject. The technician operating the MR apparatus uses such a reference scan to manually set or adjust one or more imaging parameters, including positioning of the examination subject, based on the content of the reference image. The reference image need not be of the same image quality as the diagnostic image that is subsequently generated, and thus may be acquired, for example, with lower resolution and thus with a shorter acquisition duration than is the case for the diagnostic image.

In a scan session wherein multiple MR images are acquired, it is conventional to acquire one reference image and to use the same reference image to review the imaging conditions for all of the scans throughout the session. Such a session may last up to an hour or more, and therefore it is very likely, unless patient movement is restricted in some manner, that the patient will move during the scan session. This causes the reference image, which was obtained at the beginning of the scan session, to no longer be consistent with the actual patient position that exists at a later time in the session, and therefore images obtained later in the session, wherein imaging parameters and/or the patient position have been set using this no longer accurate reference scan, may also be inaccurate.

Such a reference scan is often used in particular to set the spatial position or extent of a slice of the examination subject, from which image data are to be obtained.

Automated slice positioning techniques are known, but the same problem described above persists therein, because the reference data for the automated slice positioning technique is acquired at the beginning of the scan session, and is not repeated or adjusted during the scan session.

Motion-corrected scans are also known, wherein a real time motion correction is implemented, such as EPI and 3D PACE. In such motion-corrected scans, the reference for motion correction is typically acquired at the beginning of each motion-corrected scan. In a multi-series scan session, this means that such a motion reference is acquired a number of times that is equal to the number of scans in the scan session, which can extend the time duration of the overall session.

SUMMARY OF THE INVENTION

An object of the present invention is to provide a magnetic resonance imaging apparatus and method for implementing a scan session composed of the acquisition of multiple images, wherein a consistently valid reference scan is employed throughout the scan session, but wherein unnecessary repetitions of the acquisition of a reference scan are avoided, so that the overall duration of the scan session is only minimally extended.

The above object is achieved in accordance with the present invention in a magnetic resonance imaging method and apparatus wherein an automated decision is made, before the acquisition of data for each diagnostic image in the scan session, as to whether a previously-obtained reference scan (image) is still valid, so that the previously-obtained scan can still be used for the current diagnostic scan in the session, and thus there is no need to unnecessarily expend the time to obtain another reference scan.

If the outcome of the automated decision making procedure is that a previously-acquired reference scan, such as the immediately preceding reference scan, is still valid for use as the reference scan in the current diagnostic image data acquisition of the session, the technician then uses that previously-acquired reference scan for conducting the current diagnostic data acquisition scan.

If the automated decision procedure determines that the previously-acquired reference scan is no longer valid, such as because significant patient movement has occurred since the acquisition of that previous reference scan, and a new reference scan is then automatically implemented. That new reference scan is then used as the previously-acquired reference scan for the next diagnostic scan in the session, and so on.

The method and apparatus according to the invention thus ensure that a reference scan that is currently valid will always be used by the technician during the course of a multi-image session, but it is not necessary to repeatedly acquire such a reference scan before each and every diagnostic scan. Only if and when a previously-acquired reference scan is determined to be no longer valid is a new reference scan then implemented.

Since patient movement is the most significant factor that causes a previously-acquired reference scan to no longer be valid, in an embodiment of the invention such patient movement is cyclically or continuously monitored during the scan session, and the degree of patient movement between diagnostic image acquisitions is used as a criterion in the automated decision procedure in order to determine whether a new reference scan is necessary. If the detected degree of movement of the patient is higher than a predetermined movement threshold, the technician can be alerted, such as by a visual or audio alarm, and the technician can then make a manual check to determine whether such an extreme movement of the patient has occurred, so that repositioning of the patient is necessary.

If the detected movement is less than the predetermined threshold, the entire scan session can proceed automatically as long as no patient repositioning is required.

In a further embodiment, a new reference scan is automatically acquired before each diagnostic data acquisition. Even though in this embodiment the same number of reference scans are acquired as the number of diagnostic scans, the repeatedly acquired reference scans can be of a much lower resolution than even an initially-acquired lower resolution reference scan, so that the time for repeatedly acquiring these new reference scans is much shorter. Therefore, even though multiple reference scans are acquired during the session, it is assured that they are continually valid during the entirety of the session without extending the overall length of the session by an undesirable amount.

Again, since patient movement is the primary factor that makes a previously-acquired reference scan no longer valid, the repeatedly acquired new reference scans can be acquired with a low resolution, because such a low resolution is sufficient to determine gross patient movement by a comparison of the new reference scan with the scan that is designated as the immediately preceding reference scan (i.e., the scan that was used as the reference scan in the immediately preceding iteration, which may be the initial scan if it was determined still to be valid, or a new reference scan for the immediately preceding iteration, if such a new reference scan was acquired for that iteration).

In an embodiment, the diagnostic scans can be acquired with a first (highest) resolution that produces a diagnostic-quality image, and the initial reference scan can be acquired with a second, lower resolution that need not be acceptable for diagnostic-quality, and all subsequent reference scans can be acquired with a third (lowest) resolution, that is even lower than the second resolution, that is no higher than necessary to permit gross patient movement to be detected. In some examinations, it may not even be necessary for the initial reference scan to be acquired with the second resolution, and that initial reference scan may then also be acquired with the third (lowest) resolution.

In the first embodiment, wherein patient motion is cyclically or continuously monitored, this motion can be monitored in any suitable manner, such as by the acquisition of navigator signals or by obtaining a camera image of the patient, either as successive "snapshots" or as a continuously running video, and then comparing the snapshots, or different video frames separated by an appropriate time duration, so as to detect whether patient movement has occurred from one snapshot to the next, or from one frame to the next.

In the further embodiment wherein a new reference scan is acquired before each diagnostic scan, the most recently acquired reference scan can be automatically compared with the immediately-preceding reference scan using known pattern recognition algorithms, in order to detect whether a predetermined characteristic of the compared images exceeds a predetermined threshold, indicating that the previously-acquired reference scan is no longer valid.

DESCRIPTION OF THE PREFERRED EMBODIMENTS

Figure 1:
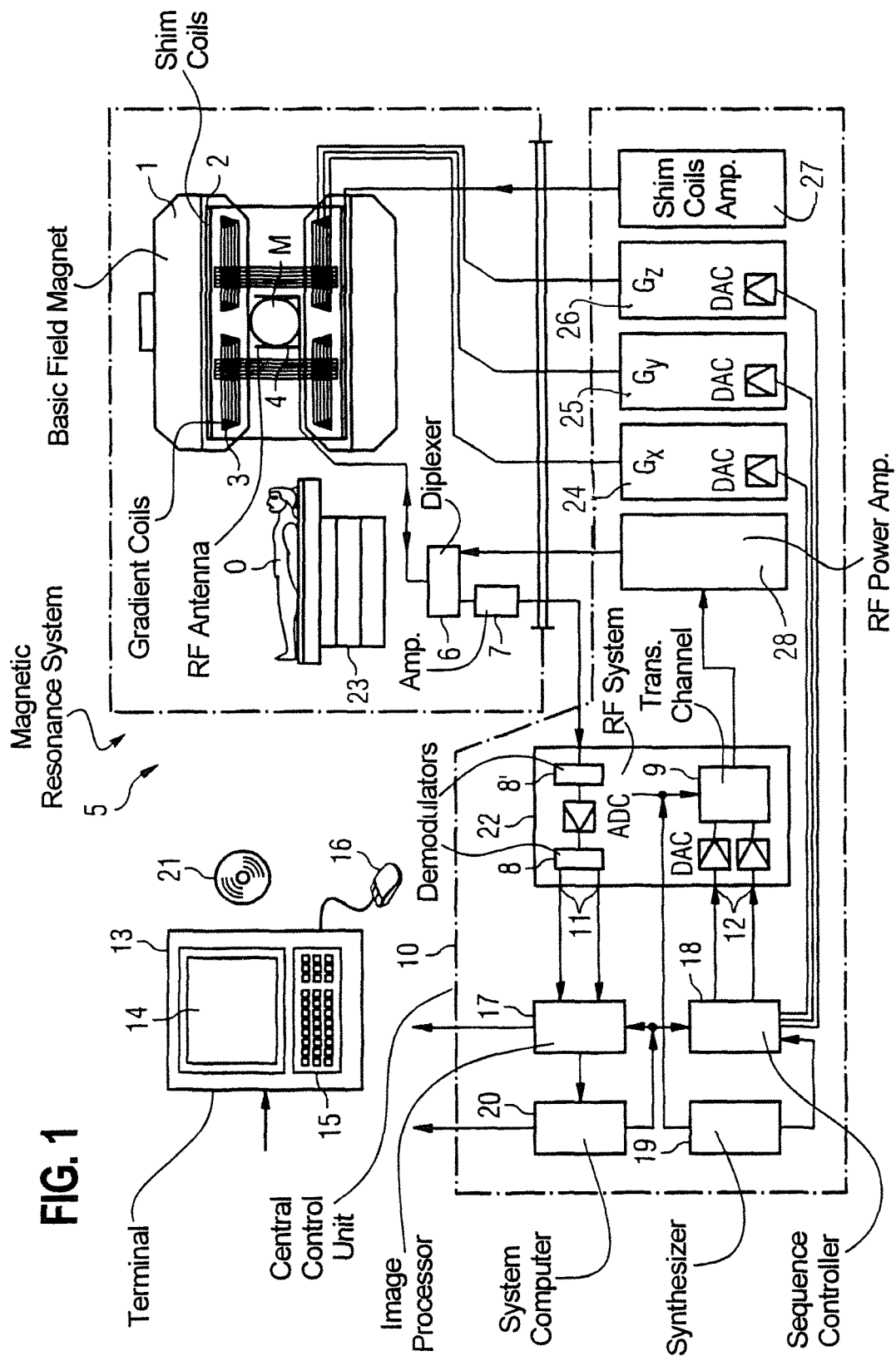
FIG. 1 schematically illustrates a magnetic resonance imaging apparatus constructed and operating in accordance with the present invention.

FIG. 1 shows a schematic representation of a magnetic resonance system 5 (a magnetic resonance imaging or magnetic resonance tomography apparatus). A basic field magnet 1 generates a temporally constant, strong magnetic field for polarization or alignment of the nuclear spins in a selected region of an examination subject O, for example of a part of a human body that is to be examined. The subject O lies on a table 23 and is examined in the magnetic resonance system 5. The high homogeneity of the basic magnetic field that is required for the magnetic resonance measurement is defined in a typically (but not necessarily) spherical measurement volume M into which the parts of the human body that are to be examined are introduced. Shim plates made of ferromagnetic material are attached at suitable points to assist the homogeneity requirements, and in particular to eliminate temporally invariable influences. Temporally variable influences are eliminated by shim coils 2, operated by shim coils amplifier 27.

A cylindrical gradient coil system 3 composed of three sub-windings is used in the basic field magnet 1. Each sub-winding is supplied with current by an amplifier to generate, for example, a linear (also temporally variable) gradient field in the respective direction of the Cartesian coordinate system. The first sub-winding of the gradient field system 3 generates a gradient $G_x$ in the x-direction; the second sub-winding generates a gradient $G_y$ in the y-direction; and the third sub-winding generates a gradient $G_z$ in the z-direction. Each amplifier has a digital/analog converter that is activated by a sequence controller 18 for accurately-timed generation of gradient pulses.

Located within the gradient field system 3 are one (or more) radio-frequency antennas 4—in particular at least one RF transmission coil and at least one RF reception coil—that convert the radio-frequency pulses emitted by a radio-frequency power amplifier 28 into an alternating magnetic field for excitation of the nuclei and alignment of the nuclear spins of the examination subject U to be examined, or of the region of the selected region O of the examination subject U that is to be examined. Each radio-frequency antenna 4 is composed of one or more RF transmission coils and multiple RF reception coils in the form of an annular—preferably linear or matrix-like—arrangement of component coils. The alternating field emanating from the precessing nuclear spins—i.e. normally the spin echo signals caused by a pulse sequence composed of one or more radio-frequency pulses and one or more gradient pulses—is also converted by the RF reception coils of the respective radio-frequency antenna 4 into a voltage (measurement signal). This signal is supplied via an amplifier 7 to a radio-frequency reception channel 8 of a radio-frequency system 22. The radio-frequency system 22 furthermore has a transmission channel 9 in which the radio-frequency pulses are generated for the excitation of the magnetic resonance. The respective radio-frequency pulses are digitally represented in the sequence controller 18 as a series of complex numbers based on a pulse sequence predetermined by the system computer 20. This number sequence is supplied as a real part and an imaginary part to a digital/analog converter in the radio-frequency system 22 via respective inputs 12, and from the digital/analog converter to the transmission channel 9. In the transmission channel 9, the pulse sequences are modulated on a radio-frequency carrier signal whose base frequency corresponds to the center frequency.

The switching from transmission operation to reception operation takes place via a transmission/reception diplexer 6. The RF transmission coils of the radio-frequency antenna(s) 4 radiate(s) the radio-frequency pulses for excitation of the nuclear spins into the measurement volume M, and resulting echo signals are scanned via the RF reception coil(s). The correspondingly acquired nuclear magnetic resonance signals are phase-sensitively demodulated to an intermediate frequency in a reception channel 8' (first demodulator) of the radio-frequency system 22 and digitized in an analog/digital converter (ADC). This signal is further demodulated to a frequency of 0. The demodulation to a frequency of 0 and the separation into real part and imaginary part occur in a second demodulator 8 after the digitization in the digital domain. A planar or three-dimensional MR image data set can be reconstructed by an image computer 17 from the measurement data acquired in such a manner. The administration of the measured magnetic resonance data, the image data and the control programs takes place via the system computer 20. Based on a specification with control programs, the sequence controller 18 monitors the generation of the respective desired pulse sequences and the corresponding scanning of k-space. In particular, the sequence controller 18 controls the accurately-timed switching of the gradients, the emission of the radio-frequency pulses with defined phase amplitude and the reception of the nuclear magnetic resonance signals.

The time base for the radio-frequency system 22 and the sequence controller 18 is provided by a synthesizer 19. The selection of appropriate control programs to generate an acquisition of magnetic resonance data (which programs are stored on a DVD 21, for example), the selection of a selected region O that should be excited and from which magnetic resonance data should be received, the specification of a substance with which the selected region O is filled to determine the flip angles for the desired signal curve, and the presentation of a generated MR image take place via a terminal 13. The terminal 13 may have a keyboard 15, a mouse 16 and a monitor 14, with which an operator can make appropriate entries in order to select a pulse sequence, in the form of an operating protocol.

Figure 2:
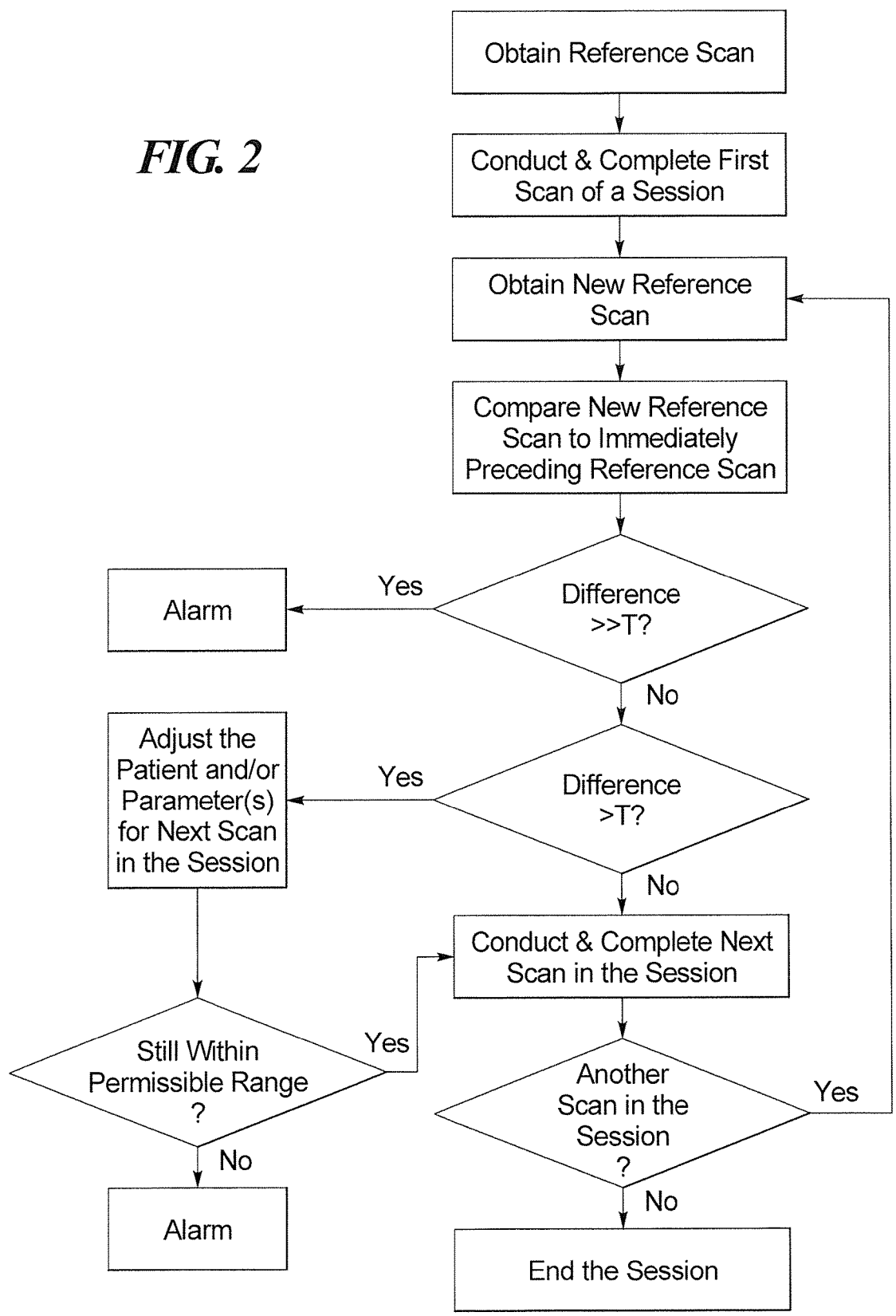
FIG. 2 is a flowchart of an embodiment of the method according to the invention.

An embodiment of the method according to the invention is shown in FIG. 2. In this embodiment, as well as in the embodiment of FIG. 3, all steps are performed by one or more of the system computer 20, the sequence controller 18 and the image processor 17. These components can be a single, commonly housed computer system, or can be distributed units connected with each other, or can be represented by distributed software.

The embodiment shown in FIG. 2 begins with obtaining a reference scan (reference image). As noted, this reference scan is of a type commonly referred to as a localizer scan or a scout scan, and is typically of a lower image quality than the diagnostic image that will subsequently be obtained, particularly in terms of resolution.

After the reference scan has been acquired the first scan (first image acquisition procedure) of a multi-scan (multi-image) session is conducted and completed. This is followed by a new reference scan then being obtained. The new reference scan is then compared to the immediately preceding reference scan which, in this initial iteration of the method, is the aforementioned initially-obtained reference scan. In subsequent iterations of the method, the "immediately preceding reference scan" will be the reference scan that was used in the immediately preceding iteration. As long as the initial reference scan is determined still to be valid in each iteration, that initial reference scan will be retained and designated as the "immediately preceding reference scan." If a new reference scan is determined to be needed, and is thus acquired, then in the next iteration that new reference scan will be (for that next iteration) the "immediately preceding reference scan."

If the comparison of the new reference scan to the immediately preceding reference scan indicates a significant difference between the two, which is much greater than a predetermined threshold value T, the technician is informed by a suitable audio or optical alarm. The threshold value T can be any suitable numerical value that can be quantified by comparing two images, and that provides a quantified measure or indicator as to whether the immediately preceding reference scan is still valid for use for acquiring the next diagnostic scan, particularly an indicator as to a degree of patient movement that has occurred between the two reference scans that are being compared.

Assuming that one of the initial localizer scans is 3D with sufficient quality to be useful for graphical slice prescription (e.g., the Siemens AutoAlign Scout) it could then be reformatted based on the found motion parameters and displayed in the GUI. This way a manual slice prescription can always be done based on images that match the position of the patient or at least it can show the current position of the patient, which could also be relevant to ensure adequate image quality.

If the difference between the compared reference scans is not so significantly greater than the threshold T as to justify the generation of an alarm (which may indicate that such a large amount of movement has occurred so that the scan session needs to be started over), the difference between the compared reference scan is then assessed to determine whether it is only modestly larger than the threshold T, i.e., movement of the patient has occurred, but the movement is sufficiently small so that this session can be continued with a reasonable adjustment of the position of the patient and/or the parameters for the next scan in the session. If the difference is greater by that amount than the threshold T, a prompt to the technician is provided, indicating the need for patient position adjustment and/or scan parameter adjustment. Once the patient adjustment and/or scan parameter adjustment has been implemented, a check is made as to whether the adjusted position and/or the adjusted parameters are still within a permissible range for continuing the session. If not, an alarm is generated to inform the technician. If conditions are still within the permissible range, the next scan in the session is conducted and completed.

In the embodiment of FIG. 2, after this next scan has been completed, a determination is made as to whether there is another scan in the session. If so, a new reference scan is obtained for the next diagnostic scan, and the aforementioned procedure is completed.

If the total number of scans designated for the session has been reached, the session is ended.

Figure 3:
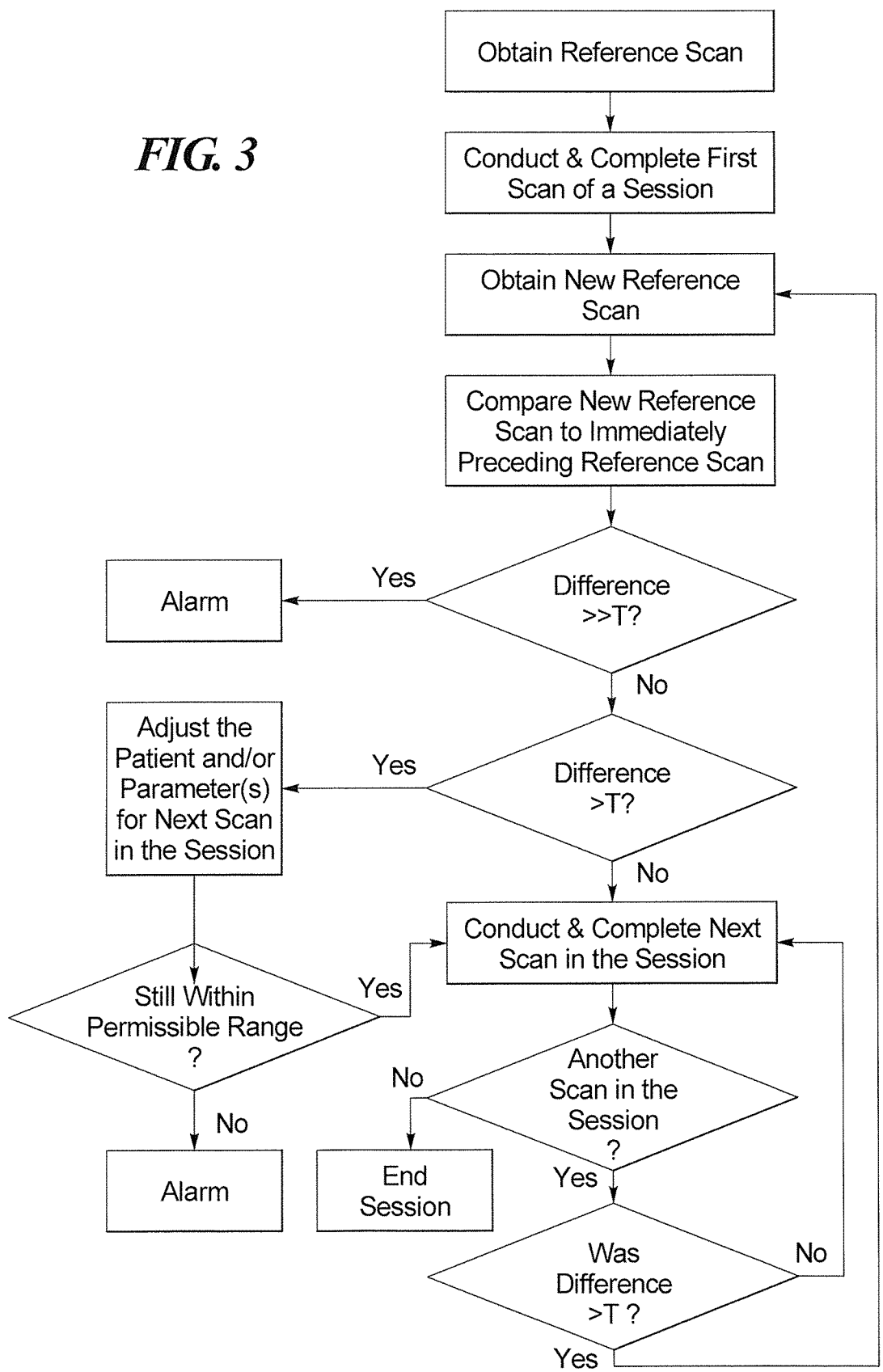
FIG. 3 is a flowchart of a further embodiment of the method according to the invention.

The embodiment shown in FIG. 3 proceeds similarly to the embodiment as shown in FIG. 2, except that a new reference scan is not automatically obtained for each and every diagnostic scan of the session. Instead, when the procedure reaches the step of conducting and completing the next scan in the session, a determination is made as to whether there is another scan in the session, and whether the difference between the compared reference scans in that iteration of the session was not greater than the threshold T. If this is the case, this indicates that the immediately preceding reference scan is still valid and thus can still be used for the next diagnostic scan, and therefore the method immediately proceeds back to the step of conducting and completing the next scan in the session.

If there was a negative answer to the aforementioned query, the method proceeds to another query as to whether there is another scan in the session and whether the difference between the compared reference scans in that iteration was greater than the threshold T, but not so substantially greater than the threshold T that an alarm was generated. If the answer to this query is "yes" then the method returns to the step of obtaining a new reference scan, and the described steps are completed again in another iteration.

Figure 4:
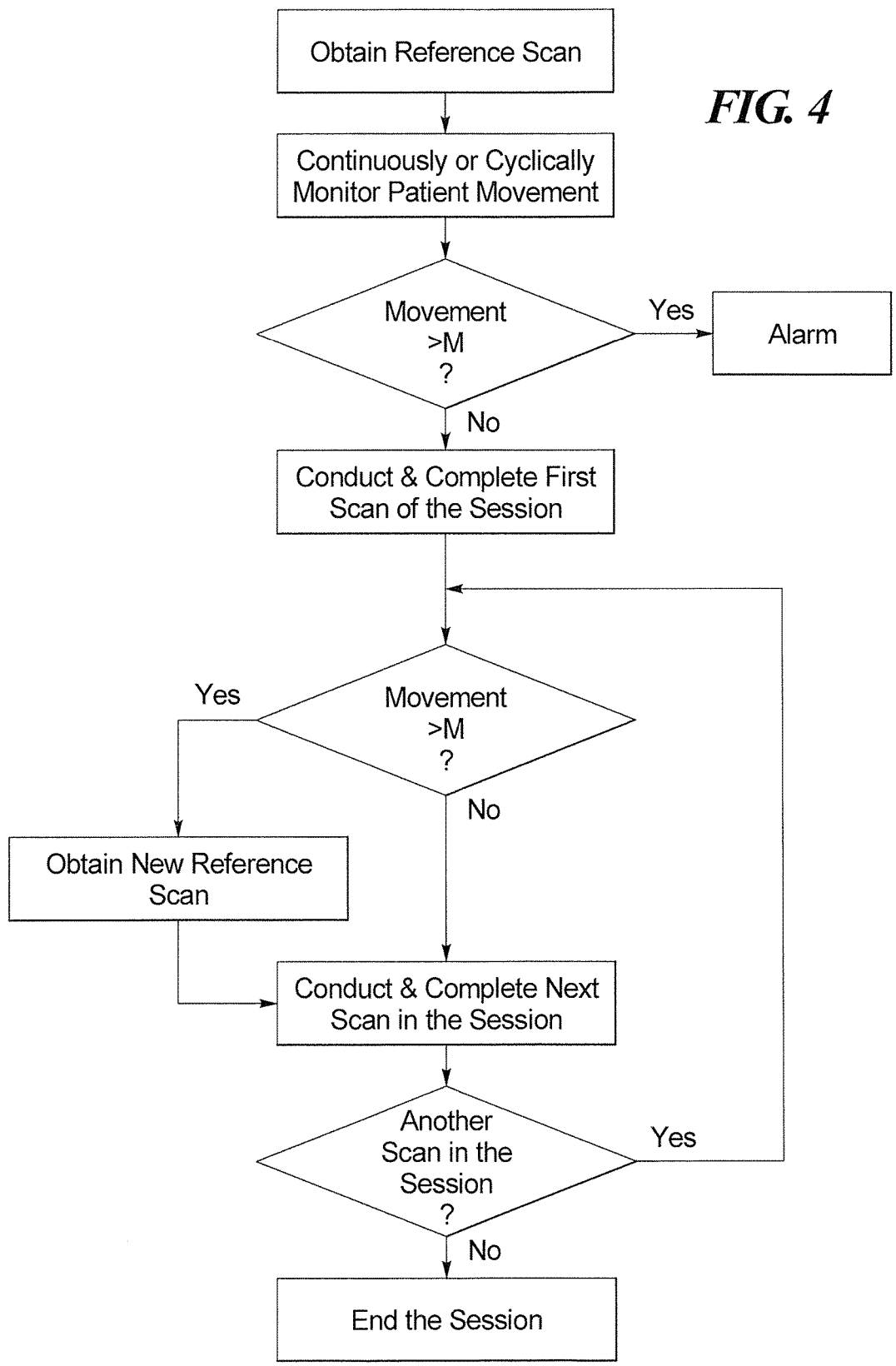
FIG. 4 is a flowchart of another embodiment of the method according to the invention.

In the embodiment shown in FIG. 4, instead of comparing two reference scans to one another in order to determine whether a valid reference scan is still available, movement of the patient is continually or cyclically monitored, such as using a navigator echo or by generating camera images. Based on this monitored patient movement, it is determined whether a previously-acquired reference scan is still usable (valid), or whether an amount of patient movement has occurred such that a new reference scan must be obtained. In this embodiment, therefore, it is always the case that a new reference scan is obtained only when necessary, i.e., only when the monitored patient movement indicates that the previously-acquired reference scan is no longer valid.

In the embodiment of FIG. 4, a reference scan is initially obtained, followed by the aforementioned continuous or cyclical monitoring of patient movement. If the result of this monitored patient movement indicates that the movement exceeds a movement threshold M, an alarm is indicated to inform the technician. If not, the first scan of the session is conducted and completed.

Thereafter, the continuously or cyclically monitored patient movement is again compared to the movement threshold M. If the monitored movement exceeds the threshold M, a new reference scan is obtained, followed by conducting and completing the next scan in the session. If the monitored movement is not greater than the movement threshold M, this indicates that the immediately preceding reference scan is still valid, and therefore the next scan in the session is conducted and completed without obtaining a new reference scan.

It is then determined whether there is another scan in the session, and if so the method returns to again check whether the monitored movement has exceeded the movement threshold M, and the aforementioned steps are repeated.

If there is no other scan in the session, the session is ended.

In all embodiments, proceeding to conduct the next scan in the session may be conditioned on it being automatically ascertained in the system computer 20 or the sequence controller 18 that a currently valid reference scan exists, either by the immediately preceding reference scan still being valid, or by a new reference scan having been obtained. In other words, the next scan in the session may be enabled only when such a currently valid reference scan exists.

Moreover, in all embodiments, it may be desirable when a new reference scan is obtained to also acquire new or updated parameter adjustment scans, such as for one or more of operating frequency, shimming or B1 mapping. If so, the same prompt to a user, or the same automatic response by the control unit, can include one or more adjustment scans.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for operating a magnetic resonance imaging apparatus, comprising:
   from a control computer, operating a magnetic resonance data acquisition unit in a scan session, in which multiple image scans of an examination subject situated in the magnetic resonance data acquisition unit will be successively obtained;
   before obtaining a first image scan of said subject in said scan session, operating said magnetic resonance data acquisition unit from said control computer to obtain an initial reference image scan of the examination subject;
   using said initial reference image scan to ensure that predetermined conditions for conducting said first image scan in said session are satisfied and, if so, operating said magnetic resonance data acquisition unit from said control computer to conduct and complete said first image scan in said session;
   before conducting each subsequent image scan in said scan session after said first scan, automatically ascertaining, in said control computer, whether a reference image scan of said subject is still a currently valid scan for conducting the respective subsequent image scan and, if so, conducting the respective subsequent image scan and, only if not, operating said magnetic resonance data acquisition unit to obtain a currently valid reference scan for the respective subsequent image scan;
   for each of said subsequent scans in said scan session, using the currently valid reference image scan for the respective subsequent image scan to ascertain, in said control computer, that predetermined respective conditions for conducting the respective subsequent image scan in said session are satisfied; and
   when said predetermined conditions for the respective subsequent image scan is ascertained in said control computer to be satisfied by using said currently valid reference image scan for the respective subsequent image scan, operating said magnetic resonance data acquisition unit from said control computer to conduct and complete the respective subsequent image scan, until all subsequent image scans in said scan session are completed.

2. A method as claimed in claim 1 comprising:
   continuously or cyclically detecting movement of said examination subject in said magnetic resonance data acquisition unit, and generating an electronic movement signal representing said movement;
   providing said movement signal to said control computer and, in said control computer, monitoring said movement of said examination subject in said magnetic resonance data acquisition unit dependent on said movement signal;
   after conducting and completing said first image scan of said scan session, automatically determining, in said control computer, whether said movement of said examination subject represented by said movement signal exceeds a predetermined movement threshold and, if not, using said reference image scan to ascertain, in said control computer, whether said conditions for conducting the respective subsequent image scan in said scan session are satisfied and, if so, automatically operating said magnetic resonance data acquisition unit from said control computer to conduct and complete said respective subsequent image scan in said scan session; and
   when said control computer determines that said movement of said examination subject exceeds said predetermined movement threshold, automatically operating said magnetic resonance data acquisition unit, from said control computer, to obtain a new reference image scan, and using said new reference image scan in said control computer as said currently valid reference image scan to ascertain whether said conditions for conducting said respective subsequent image scan in said scan session are satisfied and, if so, automatically operating said magnetic resonance data acquisition unit from said control computer to conduct and complete said respective subsequent image scan in said scan session.

3. A magnetic resonance imaging apparatus, comprising:
   a magnetic resonance data acquisition unit;

a control computer configured to operate the magnetic resonance data acquisition unit in a scan session, in which multiple image scans of an examination subject situated in the magnetic resonance data acquisition unit will be successively obtained;

said control computer being configured, before obtaining a first image scan of said subject in said scan session, to operate said magnetic resonance data acquisition unit to obtain an initial reference image scan of the examination subject;

said control computer being configured to use said initial reference image scan to ensure that predetermined conditions for conducting said first image scan in said session are satisfied and, if so, to operate said magnetic resonance data acquisition unit to conduct and complete said first image scan in said session;

said control computer being configured, before conducting each subsequent image scan in said scan session, to automatically ascertain whether a reference image scan of said subject used in an immediately preceding scan is still a currently valid scan for conducting the respective subsequent image scan and, if so, to conduct said the respective subsequent scan and, only if not, to operate said magnetic resonance data acquisition unit to obtain a currently valid reference scan for the respective subsequent image scan;

said control computer being configured, for each of said subsequent image scans in said scan session, to use the currently valid reference image scan for the respective subsequent image scan to ascertain that predetermined respective conditions for conducting the respective subsequent image scan in said session are satisfied; and said control computer being configured, when said predetermined conditions for the respective subsequent image scan is ascertained to be satisfied by using the currently valid reference image scan for the respective subsequent image scan, to operate said magnetic resonance data acquisition unit to conduct and complete the respective subsequent image scan, until all subsequent image scans in said scan session are completed.

4. An apparatus as claimed in claim 3 comprising:

a movement detector configured to continuously or cyclically detect movement of said examination subject in said magnetic resonance data acquisition unit, and to generate an electronic movement signal representing said movement and to provide said movement signal to said control computer;

said control computer being configured to monitor said movement of said examination subject in said magnetic resonance data acquisition unit dependent on said movement signal;

said control computer being configured, after conducting and completing said first image scan of said scan session, automatically determine whether said movement of said examination subject represented by said movement signal exceeds a predetermined movement threshold and, if not, use said reference image scan to ascertain whether said conditions for conducting said respective subsequent image scan in said scan session are satisfied and, if so, automatically operate said magnetic resonance data acquisition unit to conduct and complete said respective subsequent image scan in said scan session; and said control computer being configured, when said movement of said examination subject exceeds said predetermined movement threshold, to automatically operate said magnetic resonance data acquisition unit to obtain a new reference image scan, and to use said new reference image scan as said currently valid reference image scan to ascertain whether said conditions for conducting said respective subsequent image scan in said scan session are satisfied and, if so, to automatically operate said magnetic resonance data acquisition unit to conduct and complete said respective subsequent image scan in said scan session.

* * * * *